Dec. 27, 1949. J. VERCHUREN-PECHTOLD Plant Pat. 910
ROSE PLANT
Filed July 12, 1948
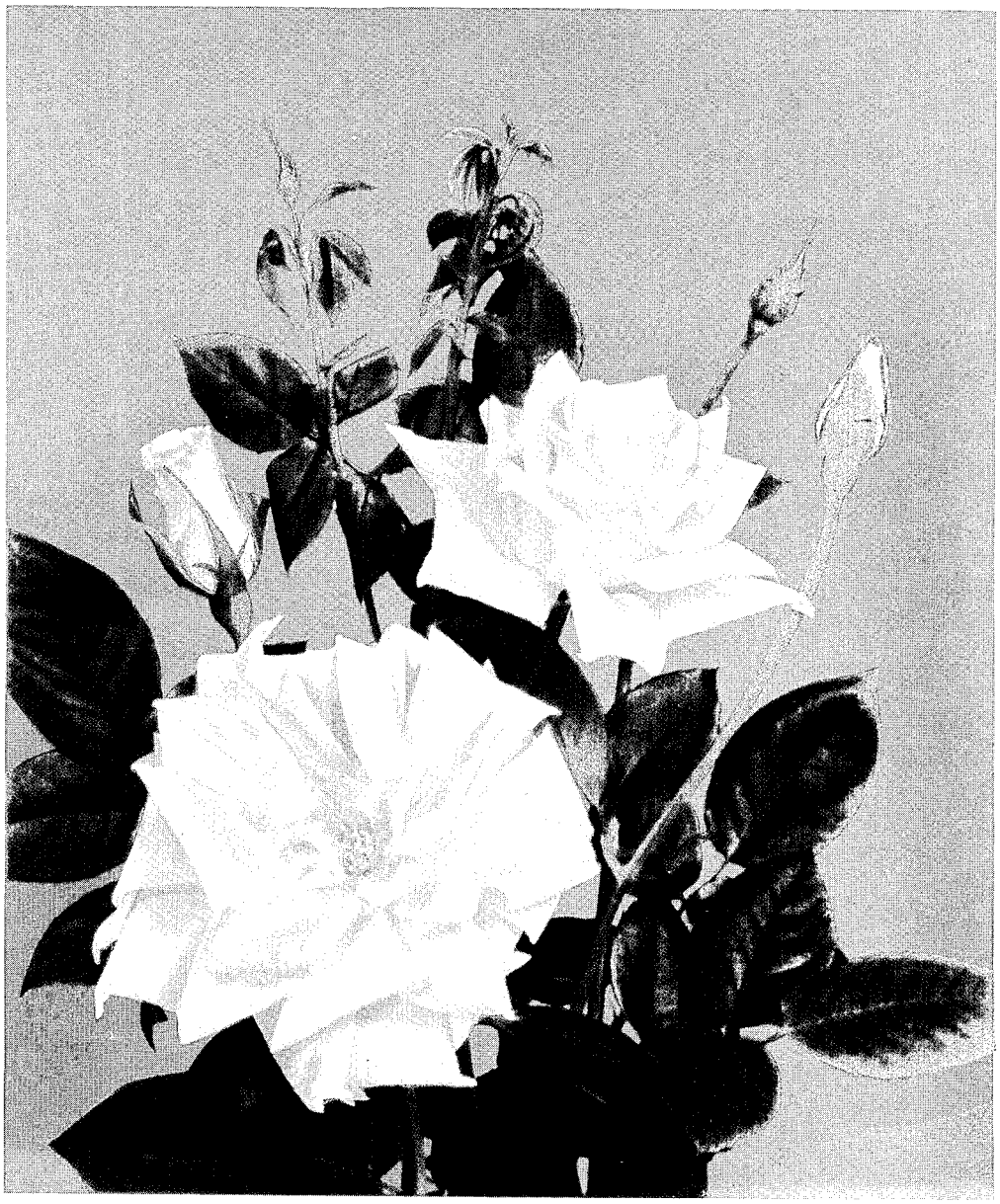
Inventor
Jac Verschuren-Pechtold,
By Hendrikus Antoine Marie Verschuren
Legal Representative of the Estate of
Jac Verschuren-Pechtold, deceased.
By Robb & Robb
Attorneys Patented Dec. 27, 1949

Plant Pat. 910

UNITED STATES PATENT OFFICE

910

ROSE PLANT

Jac. Verschuren-Pechtold, deceased, late of Haps, Netherlands, by Hendrikus Antoine Marie Verschuren, legal representative, Haps, Netherlands, assignor, by mesne assignments, to Jackson & Perkins Company, Newark, N. Y., a corporation of New York Application July 12, 1948, Serial No. 38,460

1 Claim. (Cl. 47—61)

The present invention relates to a new and distinct variety of rose plant resulting from definite efforts to produce improvements in the quality and color characteristics of a rose in the yellow range, considered by some to be the most attractive coloring for roses.

By making the particular cross, the primary objective is not only attained in respect to the color, but also a number of other desirable characters are produced, enhancing the value of this new variety in comparison with known yellow varieties, among which may be mentioned a vigorous, tall semi-branching habit of bush growth, with long shoots of flowering branches which hold the flowers without drooping; and large sized flowers developing from medium sized pointed buds and made up of thick, sun-resistant petals.

This new variety is further notable in respect to its foliage, which is glossy and well-balanced, and as to its distinctive straight thorns.

Asexual reproduction of this new variety shows the foregoing characteristics come true to form and are established.

Other details of novelty in the combinative characteristics may be noted in the following detailed description of this new variety and the accompanying drawing wherein are illustrated specimens of the flowers at different stages of development from bud to full blown flowers and of the foliage ranging from young to mature stages.

The following is a detailed description of the new variety, color terminology being in accordance with Ridgway's Color Standard:

Parentage: Seedling.
*Seed parent.*—Geheimrat Duisberg.
*Pollen parent.*—Unnamed seedling.
Classification: Hybrid tea.

*Flower*

(Observations made in the greenhouse at Newark, New York, in the month of December.)

Blooming habit: Recurrent—continuous.
Bud:
*Size.*—Medium.
*Form.*—Pointed. Is not affected by wet or hot weather.
*Color.*—When sepals first divide—Coral Red, Plate XIII, and Light Cadmium, Plate 4. When petals begin to unfurl—Light Cadmium, Plate IV. When half blown—inside of petals: Lemon Chrome, Plate IV; reverse of petals: Apricot Yellow, Plate IV.
*Sepals.*—Branched. Curl back when petals unfurl. Color — inside: Kildare Green, Plate XXXI; outside: Parrot Green, Plate VI.
*Calyx.* — Shape — apple. Size — long. Aspect—smooth. Odor when rubbed—none. Color—Parrot Green, Plate VI.
*Peduncle.*—Length—long. Aspect — prickly. Color—Cedar Green, Plate VI. Strength—erect; slender.
*Opening.*—Bud opens up well. Is not affected by adverse weather conditions.

Bloom:
*Size.*—Large. Average size when fully expanded, 4¼"–4½".
*Borne.*—Singly and several together.
*Stems.*—Long; strong.
*Form.*—When first open—high center. Permanence—retains its form to the end and flattens somewhat, but some petals stay upright and give it graceful irregular appearance.
*Petalage.*—Double (full but open center). Number of petals under normal conditions, 35–40.
*Color.*—Center of flower—Light Cadmium, Plate IV. Outer petals—Apricot Yellow, Plate IV. Base of petals (aiglet)—Lemon Chrome, Plate IV. Inside of petals—Buff Yellow, Plate IV. Reverse of petals—Apricot Yellow, Plate IV. General tonality from a distance—Apricot Yellow, Plate IV.
*Discoloration.*—General tonality at end of first day—Apricot Yellow, Plate IV. Second day—Apricot Yellow, Plate IV. Third day—Empire Yellow, Plate IV.
Petals:
*Texture.*—Thick; leathery. Is not affected by wet or hot weather.
*Appearance.* — Inside — satiny. Outside — shiny.
*Form.*—Oval.
*Arrangement.* — Imbricated (regularly arranged shingle-like). Petaloids in center—few; large.
*Persistence.*—Drop off cleanly.
*Fragrance.* — Moderate. Nature — fruity (Russet apple).
*Lasting quality.*—On plant and as cut flower—long.
Genital organs:
*Stamens, anthers.*—Large; many. Color—Cadmium Yellow, Plate III. Arrangement—regular around styles and slightly mixed with petaloids.

*Stamens, filaments (threads).*—Long. Color—Light Cadmium, Plate IV.
*Pollen.*—Color—Buff Yellow, Plate IV.
*Styles.*—Bunched, uneven length; medium length; thin.
*Stigmas.*—Color—Pinard Yellow, Plate IV.
*Ovaries.*—All inclosed in calyx.

*Plant*

Form: Bush.
Growth: Very vigorous; tall; semi-branching.
Foliage: 3 to 5 leaflets.
*Size.*—Large.
*Quantity.*—Normal.
*Color.*—New foliage—upper side: Hessian Brown, Plate XIV; under side: Hay's Russet, Plate XIV. Old foliage—upper side: Varley's Green, Plate XVIII; under side: Light Elm Green, Plate XVII.
*Shape.*—Oval.
*Texture.*—Upper side—glossy; under side—smooth. Ribs and veins—prominent.
*Edge.*—Serrated (saw toothed).
*Serration.*—Single; large.
*Leaf stem.*—Color—Parrot Green, Plate VI. Under side—smooth.
*Stipules.*—Long; smooth.
*Disease resistance.*—Good.
Wood:
*New wood.*—Color—Yellowish Oil Green, Plate V. Bark—smooth.

*Old wood.*—Color—Calla Green, Plate V. Bark—smooth.
Thorns:
*Thorns.*—Quantity—on main stalks from base and on laterals from stalk—few. Form—flat base; medium length; straight. Color when young—Hay's Russet, Plate XIV. Position—irregular.
*Prickles and needles.*—None.

It is claimed:

A new and distinct variety of rose plant characterized as to novelty by the yellow color of its flowers which carries through to the end starting with Apricot Yellow and fading to a clear Empire Yellow at the finish; the large size of the flower developing from a medium sized pointed bud; the thick, sun-resistant quality of the petals; by its vigorous, tall, semi-branching habit of growth with long shoots of flowering branches, strong enough to hold the flowers without drooping; its glossy, well-balanced foliage, and its distinctive straight thorns, substantially as shown and described.

HENDRIKUS ANTOINE
MARIE VERSCHUREN,
*Legal Representative of the Estate of Jac. Verschuren-Pechtold, Deceased.*

No references cited.